(12) United States Patent
Vistakula

(10) Patent No.: US 8,397,518 B1
(45) Date of Patent: Mar. 19, 2013

(54) APPAREL WITH INTEGRAL HEATING AND COOLING DEVICE

(75) Inventor: Kranthi K. Vistakula, Hyderabad (IN)

(73) Assignee: Dhama Innovations PVT. Ltd., Andhra Pradesh (IN)

( * ) Notice: Subject to any disclaimer, the term of this patent is extended or adjusted under 35 U.S.C. 154(b) by 0 days.

(21) Appl. No.: 13/456,584

(22) Filed: Apr. 26, 2012

(30) Foreign Application Priority Data

Feb. 20, 2012 (IN) .............................. 628/CHE/2012

(51) Int. Cl.
*F25B 21/02* (2006.01)
(52) U.S. Cl. .......................................... 62/3.5; 62/259.3
(58) Field of Classification Search ...................... 62/3.2, 62/3.3, 3.4, 3.5, 259.3, 259.4; 165/104.26, 165/185
See application file for complete search history.

(56) References Cited

U.S. PATENT DOCUMENTS

| | | | |
|---|---|---|---|
| 2,938,356 A | 5/1960 | McMahon | |
| 3,029,438 A | 4/1962 | Henschel | |
| 3,132,688 A | 5/1964 | Nowak | |
| 3,289,748 A | 12/1966 | Jennings | |
| 3,314,242 A | 4/1967 | Lefferts | |
| 3,498,077 A | 3/1970 | Gerard et al. | |
| 3,776,304 A | 12/1973 | Auerbach | |
| 4,130,902 A * | 12/1978 | Mackenroth et al. | 2/7 |
| 4,131,158 A | 12/1978 | Abhat et al. | |
| 4,483,021 A | 11/1984 | McCall | |
| 4,735,358 A * | 4/1988 | Morita et al. | 239/1 |
| D298,458 S | 11/1988 | Margolin et al. | |
| 4,920,899 A | 5/1990 | Blundy et al. | |
| 5,054,936 A * | 10/1991 | Fraden | 374/164 |
| 5,092,129 A | 3/1992 | Bayes et al. | |
| 5,097,829 A * | 3/1992 | Quisenberry | 607/105 |
| 5,269,369 A | 12/1993 | Faghri | |
| 5,532,468 A * | 7/1996 | Scofield | 235/462.37 |
| 5,720,171 A * | 2/1998 | Osterhoff et al. | 62/3.6 |
| 5,800,490 A | 9/1998 | Patz et al. | |
| 5,871,526 A | 2/1999 | Gibbs et al. | |
| 5,970,718 A | 10/1999 | Arnold | |
| 6,074,414 A | 6/2000 | Haas et al. | |
| 6,082,443 A | 7/2000 | Yamamoto et al. | |

(Continued)

FOREIGN PATENT DOCUMENTS

| | | |
|---|---|---|
| EP | 1411787 A2 | 4/2004 |
| EP | 1679984 A1 | 7/2006 |

(Continued)

OTHER PUBLICATIONS http://ideas4all.com/ideas/17163-cooling_clothes_and_accessories_based_on_the_peltier_effect_translation_of_idea_n_2762.

(Continued)

*Primary Examiner* — Mohammad Ali
(74) *Attorney, Agent, or Firm* — Goodwin Procter LLP

(57) ABSTRACT

A device for heating or cooling a body of a user is provided. The device includes a thermoelectric module, a heat sink thermally coupled to the thermoelectric module, a wetting material in thermal communication with the heat sink, and a controller for cycling the thermoelectric module in accordance with a duty cycle. Additionally, a method of heating or cooling a portion of a body of a user is provided. The method includes cycling electrical power to a thermoelectric module at a duty cycle, transferring heat from the thermoelectric module to a heat sink, and evaporating a liquid from a wetting material disposed on the heat sink. The evaporated liquid enters the surrounding atmosphere.

30 Claims, 13 Drawing Sheets

U.S. PATENT DOCUMENTS

| | | | |
|---|---|---|---|
| 6,097,088 A | 8/2000 | Sakuragi | |
| 6,125,636 A * | 10/2000 | Taylor et al. | 62/3.5 |
| 6,295,819 B1 | 10/2001 | Mathiprakasam et al. | |
| 6,341,491 B1 | 1/2002 | Paine et al. | |
| 6,393,842 B2 | 5/2002 | Kim et al. | |
| 6,430,956 B1 | 8/2002 | Haas et al. | |
| 6,495,734 B1 | 12/2002 | Fields et al. | |
| RE38,128 E * | 6/2003 | Gallup et al. | 62/3.5 |
| 6,739,138 B2 | 5/2004 | Saunders et al. | |
| 6,823,678 B1 | 11/2004 | Li | |
| 6,915,641 B2 | 7/2005 | Harvie | |
| 6,927,316 B1 | 8/2005 | Faries, Jr. et al. | |
| 6,932,150 B1 | 8/2005 | Yeh et al. | |
| 6,948,322 B1 | 9/2005 | Giblin | |
| 7,022,093 B2 | 4/2006 | Smith et al. | |
| 7,117,687 B2 | 10/2006 | Naaman | |
| 7,120,938 B2 | 10/2006 | Ichigaya | |
| 7,272,946 B2 | 9/2007 | Ichigaya | |
| 7,331,183 B2 | 2/2008 | Askew | |
| 7,559,907 B2 | 7/2009 | Krempel et al. | |
| 7,571,615 B1 | 8/2009 | Bikes | |
| 7,610,775 B2 | 11/2009 | Tonkovich et al. | |
| 7,650,757 B2 | 1/2010 | Bhatti | |
| 7,721,349 B1 * | 5/2010 | Strauss | 2/7 |
| 7,765,811 B2 | 8/2010 | Hershberger et al. | |
| 7,771,933 B2 | 8/2010 | Arciniegas et al. | |
| 7,921,473 B1 | 4/2011 | Winters | |
| 7,996,936 B2 | 8/2011 | Marquette et al. | |
| 8,001,794 B2 | 8/2011 | Windisch | |
| 2002/0026226 A1 | 2/2002 | Ein | |
| 2002/0104319 A1 * | 8/2002 | Paine et al. | 62/4 |
| 2002/0156509 A1 | 10/2002 | Cheung | |
| 2002/0170309 A1 * | 11/2002 | Strauss | 62/314 |
| 2003/0098143 A1 | 5/2003 | Winkle | |
| 2003/0110779 A1 | 6/2003 | Otey et al. | |
| 2003/0128511 A1 | 7/2003 | Nagashima et al. | |
| 2005/0000231 A1 | 1/2005 | Lee | |
| 2005/0011199 A1 * | 1/2005 | Grisham et al. | 62/3.7 |
| 2005/0153271 A1 * | 7/2005 | Wenrich | 435/1.1 |
| 2005/0174737 A1 * | 8/2005 | Meir | 361/697 |
| 2006/0180466 A1 * | 8/2006 | Dalmia et al. | 204/400 |
| 2006/0191270 A1 | 8/2006 | Warren | |
| 2006/0260183 A1 * | 11/2006 | Hockaday | 43/129 |
| 2007/0084496 A1 | 4/2007 | Edey | |
| 2007/0123758 A1 * | 5/2007 | Miesel et al. | 600/301 |
| 2007/0193278 A1 | 8/2007 | Polacek et al. | |
| 2007/0253167 A1 * | 11/2007 | Chiang | 361/717 |
| 2007/0271939 A1 | 11/2007 | Ichigaya | |
| 2008/0033518 A1 * | 2/2008 | Rousso et al. | 607/112 |
| 2008/0040831 A1 | 2/2008 | Nilforushan et al. | |
| 2008/0125747 A1 | 5/2008 | Prokop | |
| 2008/0141681 A1 * | 6/2008 | Arnold | 62/3.5 |
| 2008/0161890 A1 * | 7/2008 | Lafontaine | 607/105 |
| 2009/0179042 A1 * | 7/2009 | Milan et al. | 221/150 R |
| 2009/0306748 A1 | 12/2009 | Mollendorf et al. | |
| 2009/0308082 A1 | 12/2009 | Monk | |
| 2009/0312823 A1 * | 12/2009 | Patience et al. | 607/104 |
| 2010/0005572 A1 | 1/2010 | Chaplin | |
| 2010/0084125 A1 * | 4/2010 | Goldstein et al. | 165/287 |
| 2010/0107657 A1 * | 5/2010 | Vistakula | 62/3.5 |
| 2010/0132100 A1 | 6/2010 | Courtney et al. | |
| 2010/0198322 A1 | 8/2010 | Joseph et al. | |
| 2010/0281883 A1 | 11/2010 | Romano | |
| 2010/0294455 A1 | 11/2010 | Yang et al. | |
| 2011/0079022 A1 * | 4/2011 | Ma et al. | 62/3.2 |
| 2011/0144723 A1 * | 6/2011 | Streeter et al. | 607/88 |

FOREIGN PATENT DOCUMENTS

| | | |
|---|---|---|
| EP | 1737052 A1 | 12/2006 |
| JP | 2047327 A | 2/1990 |
| JP | 4209807 A | 7/1992 |
| JP | 9327614 A | 12/1997 |
| JP | 2001040512 A | 2/2001 |
| JP | 2009097106 A | 5/2009 |
| JP | 2010018938 A | 1/2010 |
| WO | WO-0229348 A1 | 4/2002 |
| WO | WO-2004014169 A2 | 2/2004 |
| WO | WO-2004111741 A1 | 12/2004 |
| WO | WO-2005081679 A2 | 9/2005 |
| WO | WO-2006086618 A1 | 8/2006 |
| WO | WO-2008103742 A2 | 8/2008 |

OTHER PUBLICATIONS http://weightweenies.starbike.com/forum/viewtopic.php?f=3&t=61242&start=0.

http://arbroath.blogspot.com/2011/05/indian-inventor-develops-clothes-to.html.

International Search Report and Written Opinion for PCT/US2008/054438 mailed Jul. 17, 2008 (5 pages).

* cited by examiner

APPAREL WITH INTEGRAL HEATING AND COOLING DEVICE

CROSS-REFERENCE TO RELATED APPLICATION

This application claims priority to Indian Patent Application No. 628/CHE/2012, filed Feb. 20, 2012.

FIELD OF THE INVENTION

This invention relates generally to devices and methods for heating or cooling an object and, more particularly, to devices and methods that utilize a thermoelectric module to heat or cool a body part of a user.

BACKGROUND OF THE INVENTION

Thermo-regulated apparel is apparel that includes a thermal device for adding or removing heat from a body of a wearer. Thermo-regulated apparel may be implemented in a wide-variety of products and has many uses. For example, a thermo-regulated jacket may keep a person warm on a cold day or cool on a hot day. Likewise, a thermo-regulated brace or bandage may be used to cool a body part (e.g., to reduce swelling after an injury) or heat a body part (e.g., to relieve muscle pain).

Thermo-regulated apparel may be categorized as either active or passive. Active thermo-regulated apparel may be used to maintain a temperature set by the wearer. Conventional thermal devices used in active thermo-regulated apparel include resistive heaters for heating and compressive coolers for cooling. By contrast, passive thermo-regulated apparel is capable of simply adding or removing heat, without maintaining a desired temperature. Conventional thermal devices used for passive thermo-regulated apparel include chemical reaction systems for heating and phase change materials for cooling. Conventional thermal devices for both active and passive thermo-regulated apparel are capable of either heating or cooling, but not both heating and cooling.

One type of thermal device for thermo-regulated apparel is a powered thermoelectric device. A thermoelectric device is a heat pump that transfers heat from a cold side of the device to a hot side of the device, with consumption of electrical energy. Thermoelectric devices are desirable, because they allow precise control over heat transfer rates, and they are capable of providing both heating and cooling. To maintain desired surface temperatures, however, heat must generally be dissipated from the hot side of the thermoelectric device.

Previous attempts to dissipate heat from thermoelectric devices in thermo-regulated apparel have been largely unsuccessful. One reason for this difficulty is that the insulating properties of apparel make it difficult to transfer heat through the apparel to the surroundings. Further, to achieve adequate heat dissipation by natural or forced convection, the thermoelectric module must generally placed on an exterior portion of the apparel, which may be unattractive, cumbersome, and unsuitable for active use. Achieving sufficient heat dissipation rates through radiative heat transfer, forced convection, and/or phase change materials may not be feasible.

There is a need for thermo-regulated apparel that is capable of providing sufficient rates of both heating and cooling. In particular there is a need for thermo-regulated apparel that includes a thermoelectric device and is capable of adequately dissipating heat from the hot side of the device, while remaining attractive and suitable for active use.

SUMMARY

The devices and methods described herein provide thermo-regulated apparel for heating and/or cooling at least a portion of the body of a wearer. Compared to previous designs, the devices described herein include a heat sink that is amongst the lightest of its kind A thickness of the heat sink is optimized for very high lateral heat transfer, and surface textures on the heat sink provide optimized heat dissipation rates. A wetting material disposed on the heat sink is configured to hold a desired amount of cooling liquid (e.g., water), without adding an excessive heat transfer resistance or heat capacity. By optionally cycling the electrical power supplied to the thermoelectric device, desired rates of heating and/or cooling are achieved, and the user's perception of the heating and/or cooling is enhanced. The devices and methods described herein provide efficient heating and/or cooling for a wide variety of applications and items of apparel, including jackets, boots, helmets, bandages, and braces.

In one aspect, the invention relates to a device for heating or cooling a body of a user. The device includes a thermoelectric module, a heat sink thermally coupled to a surface of the thermoelectric module, a wetting material in thermal communication with the heat sink, and a controller for cycling the thermoelectric module in accordance with a duty cycle, for example, a duty cycle greater than about 10%.

In certain embodiments, the device includes a supply tank and a supply line connecting the wetting material and the supply tank. The supply line may include a wicking material to convey a liquid from the supply tank to the wetting material. A thickness of the heat sink may be from about 1 mm to about 15 mm. In one embodiment, the device includes a binding layer securing the wetting material to the heat sink (e.g., the wetting material may be disposed between the heat sink and the binding layer). The binding layer may be wrapped around an outer edge of the heat sink.

In certain embodiments, the heat sink includes an etched surface and/or a contoured surface. The contoured surface may form a bend having a bend angle in a range from about 0 degrees to about 90 degrees. In one embodiment, the wetting material includes an antimicrobial agent. In another embodiment, the wetting material includes a hydrophilic material. A thickness of the wetting material may be from about 1 mm to about 3 mm. The wetting material may include tissue and/or cotton.

In certain embodiments, the device includes a battery and a switched electrical connection. The device is typically integrated into apparel, such as a neck wrap, an elbow pack, a knee pack, a back pack, an ankle pack, a universal pack a heating jacket, a cooling jacket, a heating-cooling jacket, an anti-bleeding pack, a head band, an abdominal pad, a shoe insole, clothing, footwear, a car seat, and/or a helmet. In one embodiment, the thermoelectric module includes a heating surface area from about 100 mm$^2$ to about 2000 mm$^2$.

In another aspect, the invention relates to a method of heating or cooling a portion of a body of a user. The method includes the steps of: cycling electrical power to a thermoelectric module at a duty cycle of at least about 10%; transferring heat from the thermoelectric module to a heat sink; and evaporating a liquid from a wetting material disposed on the heat sink, wherein the evaporated liquid enters the surrounding atmosphere.

In certain embodiments, the method includes conveying the liquid from a supply tank to the wetting material by, for example, wicking the liquid through a wicking material disposed within a supply line. In one embodiment, the method includes applying the liquid to the wetting material (e.g., by spraying or dripping). In another embodiment, cycling electrical power includes a duty cycle from about 30% to about 100%. A cycle time for cycling electrical power may be from about 1 minute to about 10 minutes.

In certain embodiments, transferring heat from the thermoelectric module includes a heat transfer rate from about 0.2 W to about 200 W. Likewise, a heat transfer rate associated with evaporating the liquid from the wetting material may be from about 0.2 W to about 200 W. A cold side of the thermoelectric module may have a temperature from about −10 degrees C. to about 30 degrees C. In one embodiment, the heat sink temperature is at least about 30 degrees C.

In certain embodiments, the method includes treating a disorder such as arthritis, tennis elbow, golf elbow, a migraine headache, menstrual pain, back pain, and/or an ankle sprain. In one embodiment, the method includes providing electrical stimulation to a user. The liquid may include a fragrance to provide aromatherapy.

In another aspect, the invention relates to a method of manufacturing a device for heating or cooling at least a portion of a body of a user. The method includes the steps of: providing and etching a surface of a heat sink with an etching agent to increase an effective surface area thereof; attaching the heat sink to a thermoelectric module; disposing a wetting material over the heat sink; and securing the wetting material to the heat sink with a binding layer.

In certain embodiments, the wetting material is disposed between the heat sink and the binding layer. The method may include introducing into the heat sink a bend angle from about 10 degrees to about 90 degrees. Securing the wetting material may include wrapping the binding layer around an edge of the heat sink. In one embodiment, the method includes electrically connecting the thermoelectric module to a battery pack. The thermoelectric module is typically integrated into an item of apparel, such as a neck wrap, an elbow pack, a knee pack, a back pack, a heating jacket, a cooling jacket, a heating-cooling jacket, an anti-bleeding pack, a head band, an abdominal pad, a shoe insole, clothing, footwear, a car seat, and/or a helmet.

DESCRIPTION OF DRAWINGS

Other features and advantages of the present invention, as well as the invention itself, may be more fully understood from the following description of the various embodiments, when read together with the accompanying drawings, in which.

DETAILED DESCRIPTION

It is contemplated that systems, devices, methods, and processes of the claimed invention encompass variations and adaptations developed using information or the teachings from the embodiments described herein. Adaptation and/or modification of the devices, systems, methods, and processes described herein may be performed by those of ordinary skill in the relevant art and all are considered to be within the scope of the invention.

Throughout the description, where systems are described as having, including, or comprising specific components, or where processes and methods are described as having, including, or comprising specific steps, it is contemplated that, additionally, there are systems of the present invention that consist essentially of, or consist of, the recited components, and that there are processes and methods according to the present invention that consist essentially of, or consist of, the recited processing steps.

It should be understood that the order of steps or order for performing certain actions is immaterial, so long as the invention remains operable. Moreover, two or more steps or actions may be conducted simultaneously.

The mention herein of any publication is not an admission that the publication serves as prior art with respect to any of the claims presented herein. The Background section is presented for purposes of clarity and is not meant as a description of prior art with respect to any claim.

Apparel with heating and cooling capabilities is described in International Patent Application No. PCT/US2008/054438, filed Feb. 20, 2008, titled "Apparel with Heating and Cooling Capabilities," and in International Patent Application No. PCT/IN2011/000438, filed Jul. 1, 2011, titled "Article of Clothing for Heating or Cooling Body of Wearer," the disclosures of which are hereby incorporated by reference herein in their entireties.

Figure 1:
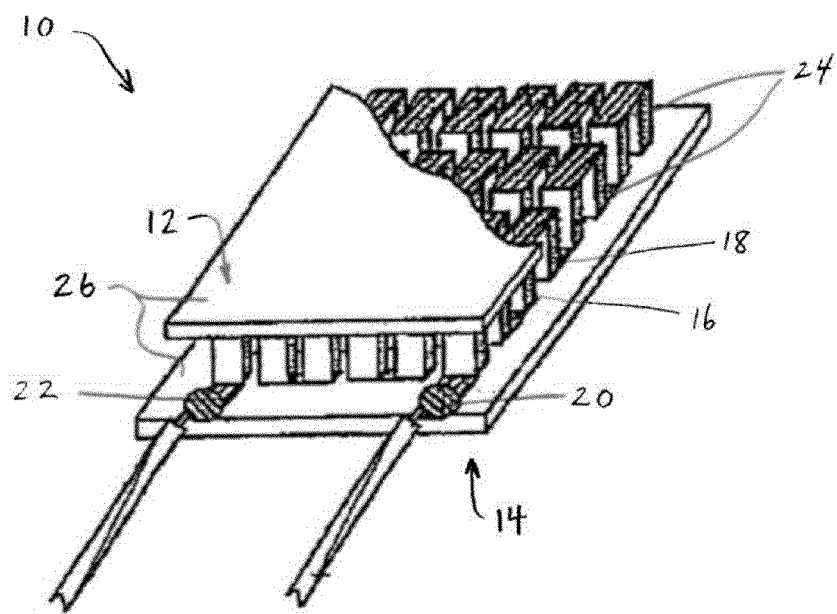
FIG. 1 is a schematic perspective view of a conventional thermoelectric module for use with various embodiments of the invention.

Referring to FIG. 1, a thermoelectric module (TEM) 10 is a solid-state heat pump that transfers heat from a cold side 12 of the TEM 10 to a hot side 14 of the TEM 10, against a temperature gradient, with consumption of electrical energy, using the Peltier effect. A standard single-stage TEM can achieve temperature differentials of up to 70° C.

When the TEM 10 is used for cooling, heat is absorbed at the cold side 12 by electrons as they pass from a low energy level in a p-type semiconductor element 16 to a higher energy level in an n-type semiconductor element 18. A supplied voltage between a positive connector 20 and a negative connector 22 provides electrical potential to move the electrons through the TEM 10. At the hot side 14, energy is expelled to a heat sink as electrons move from the higher energy level n-type semiconductor element 18 to the low energy level p-type semiconductor element 16. As depicted, conductive layers 24 are placed above and below the semiconductor elements 16, 18. Electrical insulator layers 26 are placed outside of the conductive layers 24 and form the cold side 12 and the hot side 14.

TEMs have several advantages over other heating and cooling devices. For example, TEMs have a solid state construction with no moving parts and are therefore generally more reliable. TEMs are also capable of cooling to well below ambient temperature (e.g., as low as minus 100° C., using multistage TEMs). Further, TEMs may be switched from heating to cooling (or cooling to heating) by simply reversing the polarity of the electrical supply. TEMs also may enable temperatures to be controlled precisely (e.g., within ±0.01° C.) and maintained under steady-state conditions. In a heating mode, TEMs are generally more efficient than conventional resistance heaters, because they generate heat from the electrical power and from the heat pumping action that occurs.

A heat sink is an object that transfers thermal energy from a higher temperature to a lower temperature fluid medium. The fluid medium is frequently air, but may also include or be water and/or other liquids, such as refrigerants and/or oils. Well-known examples of heat sinks include car radiators and heat exchangers used in refrigeration and air conditioning systems. Heat sinks are often used to cool electronic and optoelectronic devices, such as higher-power lasers and light emitting diodes (LEDs).

Figure 2:
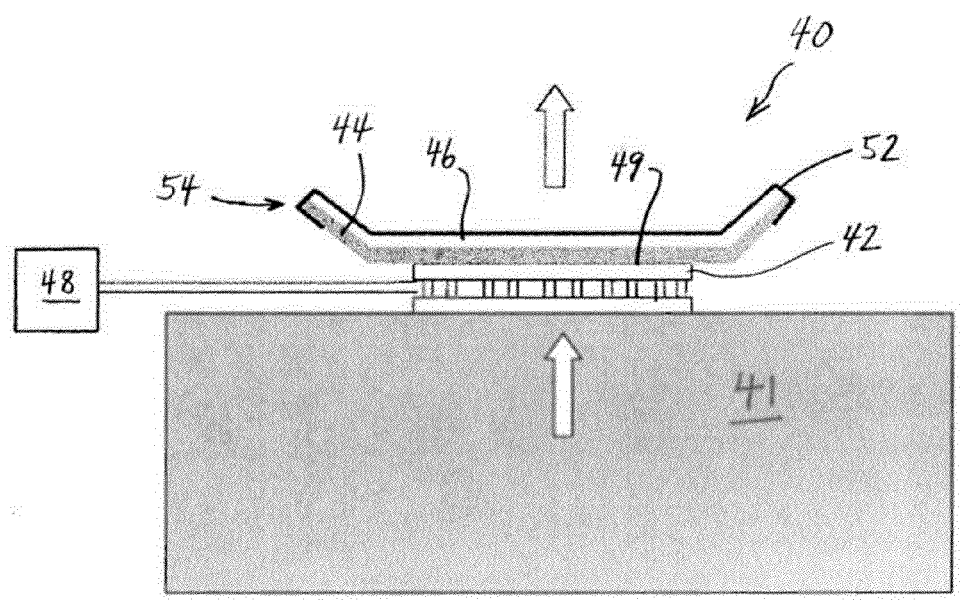
FIG. 2 is a schematic side view of a device for heating or cooling a body of a wearer, in accordance with one embodiment of the invention.

Referring to FIG. 2, in certain embodiments, a device 40 for heating and/or cooling an object, such as a body part 41 of a user, includes a TEM 42, a heat sink 44, a wetting material 46, and a controller 48 with a power source. As depicted, the heat sink 44 is thermally coupled to a top or hot side 49 of the TEM 42 using, for example, a conductive grease or adhesive, such as silver thermal epoxy and/or aluminum thermal epoxy, and/or thermal pads. The wetting material 46 is disposed on or covering at least a portion of a wet side 50 of the heat sink 44. A binding layer 52 (e.g., an aluminum mesh, a polyester mesh, and/or a nylon mesh or the like breathable structure) is placed over the wetting material 46 and can be wrapped around an edge 54 of the heat sink 44. A power supply provides D.C. electrical power to the TEM 42. The controller 48 controls the amount of electrical power delivered to the TEM 42, according to a desired amount of cooling or heating. When the device 40 is used for cooling, heat is transferred out of the body part 41, through the TEM 42, and into the heat sink 44, where heat transfer to the surroundings may occur.

Figure 3:
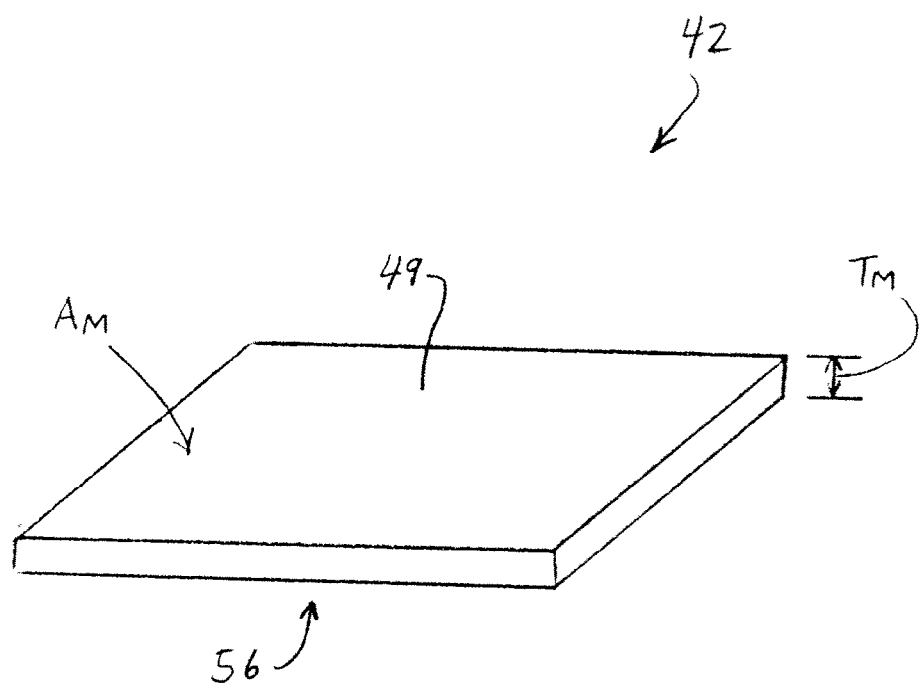
FIG. 3 is a schematic perspective view of a thermoelectric module, in accordance with an embodiment of the invention.

Referring to FIG. 3, in certain embodiments, the TEM 42 is substantially flat and has a substantially uniform thickness $T_M$. The thickness $T_M$ may be, for example, about 4 mm, or from about 1 mm to about 10 mm. In alternative embodiments, the TEM 42 is curved (i.e., not flat) to, for example, more closely follow a surface contour of the body part and/or provide a desired heat transfer pattern. As depicted, the hot side 49 and a cold side 56 of the TEM 42 may be approximately rectangular, although the hot and cold sides 49, 56 may have any geometric shape (e.g., circular, triangular, rectangular, hexagonal, etc.). A surface area $A_M$ of each of the hot and cold sides 49, 56 may be, for example, from about 450 mm$^2$ to about 900 mm$^2$, or from about 100 mm$^2$ to about 2000 mm$^2$. In various embodiments, a cooling capacity of the TEM 42 is about 25 W, or from about 0.1 W to about 50 W. The surface area $A_M$ and cooling capacity of the TEM 42 are chosen according to the desired amount of cooling or heating to be achieved. In one embodiment, the TEM 42 includes bismuth telluride pellets and $Al_2O_3$ ceramic cover plates.

Figure 4:
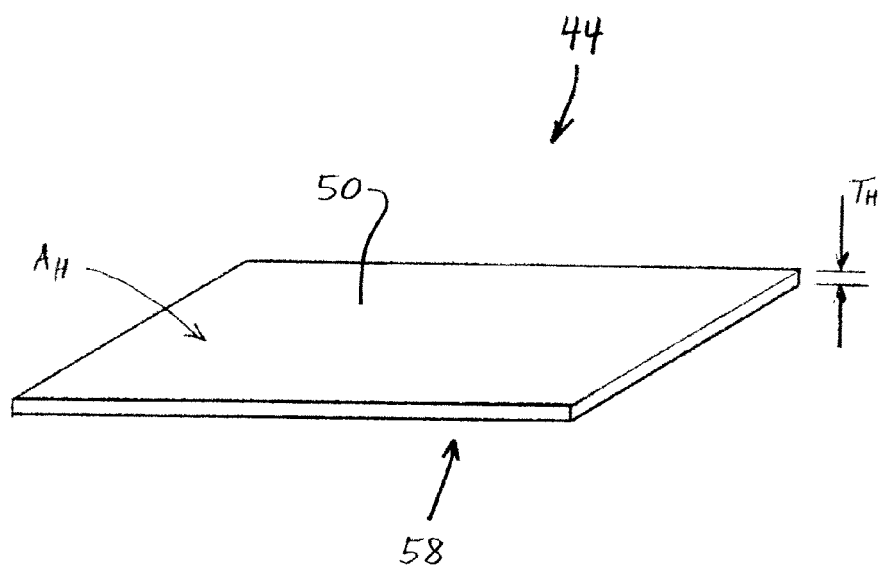
FIG. 4 is a schematic perspective view of a heat sink, in accordance with an embodiment of the invention.

Referring to FIG. 4, in certain embodiments, the heat sink 44 is a thin sheet or plate having the wet side 50 and a dry side 58. A thickness $T_H$ of the heat sink 44 may be, for example, about 2 mm, or from about 1 mm to about 15 mm. The thickness $T_H$ of the heat sink 44 may be optimized to allow efficient conductive heat transfer in a lateral direction through the heat sink 44 (i.e., in a direction parallel to the wet and dry sides 50, 58). The wet and dry sides 50, 58 may each have a surface area $A_H$ of, for example, about 2500 mm$^2$, or from about 100 mm$^2$ to about 10,000 mm$^2$. In various embodiments, the heat sink 44 is the lightest of its kind, having a weight from about 1 g to about 500 g.

The heat sink 44 may be made of any material capable of providing the desired heat transfer to or from the TEM. In certain embodiments, the heat sink 44 includes a metal, carbon fiber, and/or a polymer. Examples of suitable metals include magnesium, aluminum, copper, aluminum alloys of various grades, bonded metals, and/or anodized materials. The heat sink 44 may include, for example, bonded aluminum with copper. In one embodiment, the heat sink 44 includes phase change materials and/or solid polymers having hydrogen bonds that break upon heating and reform upon removal of heat. The heat sink 44 may include one or more fins for heat removal. In certain embodiments, the heat sink 44 is filled with a liquid, such as water and/or alcohols.

Figure 5:
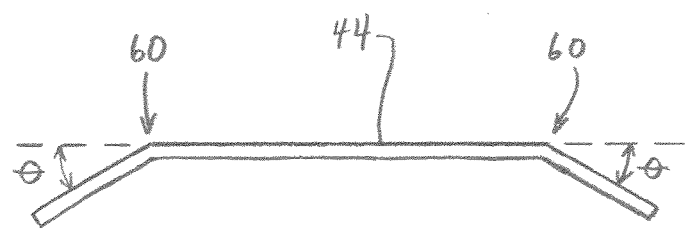
FIG. 5 is a schematic side view of a heat sink having a bend angle, in accordance with an embodiment of the invention.
Figure 6:
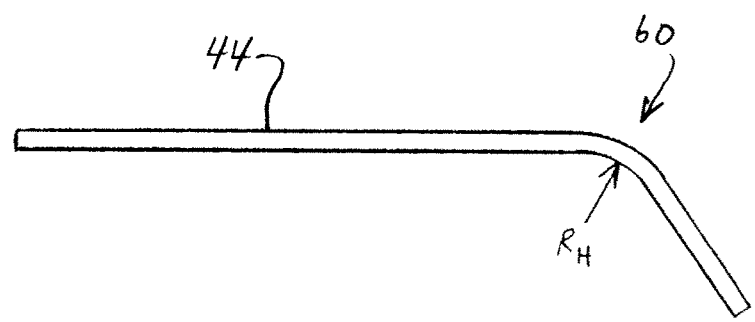
FIG. 6 is a schematic side view of a heat sink having a bend with a radius of curvature, in accordance with an embodiment of the invention.

Referring to FIG. 5, the heat sink 44 may be contoured and/or include one or more bends 60. A bend angle θ of a bend 60 may be, for example, from about 30° to about 45°. In one embodiment, the bend angle θ is up to about 90° (or down to about)-90°. As depicted, the bend angle θ allows the heat sink 44 to more closely approximate the shape of the body part. In one embodiment, the bend angle θ improves heat transfer to or from the heat sink 44. Referring to FIG. 6, a radius of curvature $R_H$ of the bends 60 in the heat sink 44 may be, for example, from about 0 mm to about 50 mm, or from about 2 mm to about 10 mm.

In general, the heat sink 44 is geometrically optimized to achieve a desired steady state rate of cooling, based on the size and power consumption of the TEM 42. For example, the heat sink thickness $T_H$ and bend angle θ are optimized to conduct heat in a lateral direction through the heat sink, away from the TEM 42, even when the TEM surface area $A_M$ is much smaller than the heat sink surface area $A_H$. In certain embodiments, a high thermal conductivity of the heat sink 44 results in a temperature distribution within the heat sink 44 that is nearly uniform (i.e., less than about 1° C. of temperature variation). The heat sink 44 may be of any shape, such as square, rectangular, circular, triangular, hexagonal, etc., or combinations thereof. In one embodiment, the heat sink is shaped to conform generally to the body of the wearer.

In various embodiments, one or more surfaces of the TEM 42 and/or the heat sink 44 include a surface roughness that promotes heat transfer to and/or from the one or more surfaces of the TEM 42 and heat sink 44. For example, a surface roughness $R_a$ of the TEM 42 and/or the heat sink 44 may be from about 10 microns to about 1000 microns. In one embodiment, the TEM 42 and heat sink 44 are treated with an etching agent, which may be alkaline or acidic (e.g., sodium hydroxide or sulfuric acid), to achieve the desired surface texture or roughness. The etching agent may also remove undesirable oxide layers from surfaces of the TEM 42 and/or heat sink 44. A pH of the etching agent may be, for example, from about 10 to about 12. The TEM 42 and/or the heat sink 44 may be exposed to the etching agent for, for example, about 15 minutes, or from about 1 minute to about 100 minutes. The etched surface of the heat sink 44 may improve bonding to the TEM 42, as well as enhance heat transfer to the liquid in the proximate wetting material 46.

In certain embodiments, the wetting material 46 is a material that absorbs or is wet by a cooling liquid, such as water, alcohol, or mixtures thereof. The wetting material 46 may be a hydrophilic material, such as tissue (e.g., a cellulose or paper-based facial tissue), cotton (e.g., a gauze pad or portion thereof for wound dressing), combinations of tissue and cotton, cellulosic materials, foam materials, polymer water soaking materials, and/or water soaking fabrics. For example, the wetting material may include about 10 layers of tissue and/or cotton, or from about 1 layer to about 20 layers of tissue and/or cotton. In certain embodiments, each layer of tissue and/or cotton has a thickness of about 1 mm, or from about 0.5 mm to about 3 mm. The wetting material is configured to hold an optimized amount of cooling liquid for evaporative cooling without acting as a significant thermal insulator or providing a substantial thermal mass or heat capacity. In one embodiment, the wetting material 46 is firmly attached to the heat sink using the binding layer 52.

To prevent the growth of mold or other microbes, the wetting material 46, binding layer 52, and/or other materials or surfaces of the device may include an antimicrobial agent. In one embodiment, the antimicrobial agent includes silver (e.g., silver particles) and/or a pyrithione salt (e.g., zinc pyrithione).

In certain embodiments, the controller 48 is used to adjust the amount of heating or cooling achieved by the TEM 42. In general, the controller 48 achieves this by increasing or decrease the electrical energy applied to the TEM 42. For example, the controller 48 may increase or decrease the applied electrical current and/or voltage. The electrical current applied to the TEM 42 may be, for example, about 1.7 Amps, or from about 0.2 Amps to about 5 Amps. The voltage applied to the TEM 42 may be, for example, about 7.4 V, or from about 2 V to about 35V. The power source may be batteries or line power conditioned with a suitable transformer.

Figure 7:
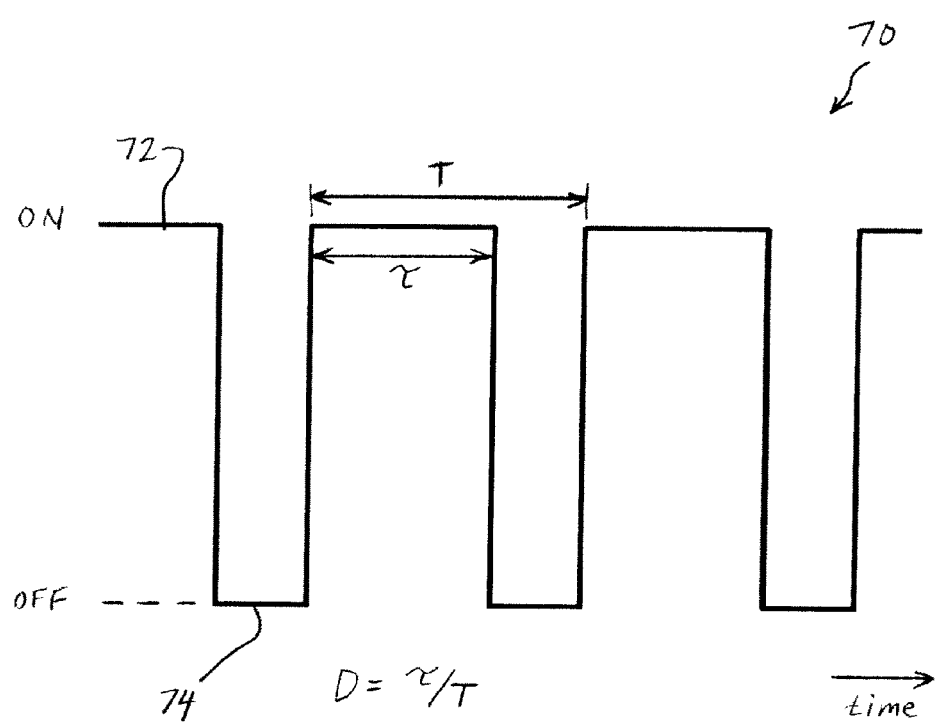
FIG. 7 is a schematic view of a rectangular waveform having a duty cycle, in accordance with an embodiment of the invention.

In certain embodiments, the controller 48 achieves the desired heating or cooling by cycling the electrical current and/or voltage on and off (or between higher and lower values) at a desired duty cycle and period. FIG. 7 is a graphical depiction of a rectangular waveform 70, in accordance with one embodiment of the present invention. As depicted, the waveform 70 oscillates between an on or higher state 72 and an off or lower state 74 at a period T. Within each oscillation, the waveform 70 is in the on state for a duration $\tau$. In certain embodiments, a duty cycle D for the waveform 70 is the ratio of duration $\tau$ to period T (i.e., D=$\tau$/T). The duty cycle D and period T chosen and implemented by the controller 48 depend on the particular cooling or heating application. For example, in knee pack or elbow pack applications, it may be desirable to use a duration $\tau$ of about 3 min and a period T of about 3 minutes and six seconds. In a neck scarf cooling application, it may be desirable to use a duration $\tau$ of about 8 seconds and a period T of about 14 seconds, or a duration $\tau$ of about 30 seconds and a period T of about 35 seconds. In certain embodiments, the period T may be, for example, about 3 minutes, from about 2 minutes to about 5 minutes, or from about 1 minute to about 10 minutes. The duty cycle D may be up to about 100%. For example, the duty cycle D may be from about 10% to about 100%. In one embodiment, the duty cycle D is about 97%. In general, a higher duty cycle D results in more electrical energy consumption and therefore more heating or cooling. It has been discovered that the highly effective heat transfer capabilities of the wetted heat sink and overall configuration of the device 40 make higher duty cycles both achievable and beneficial to the user. The device 40 is not limited by the ability to reject heat from the heat sink 44 to ambient, thus providing a much more compact, lightweight and energy efficient device 40 than conventional systems. Similar benefits are achieved when operated in reverse to provide heating comfort to the user.

In addition to controlling the rate of heating and/or cooling, one advantage of cycling the electrical power, as described above, is that it may enhance the user's perception of the heating and/or cooling. For example, after a few minutes of steady heating or cooling without cycling the electrical power, the user may not be able to detect that he or she is being heated or cooled. By contrast, when the electrical power is cycled at the duty cycle D, the user is more likely to perceive the heating or cooling, thereby enhancing the user's experience with the device. For example, a period T of about 2-4 minutes has been found to provide optimal perception of heating and/or cooling by the user.

In various embodiments, the device 40 is incorporated into an item of apparel. The item of apparel may be, for example, an item that is worn by a user and/or an item that may be attached to the user or otherwise come into contact with the user. For example, the item of apparel may be a neck wrap (e.g., a scarf), an elbow pack, a knee pack, a back pack, an ankle pack, a universal pack, a heating jacket, a cooling jacket, a heating-cooling jacket, an anti-bleeding pack, a head band, a helmet, an abdominal pad, a shoe insole, clothing, footwear (e.g., athletic shoes, and/or boots), a chair, a seat (e.g., a car seat), a steering wheel, and/or an armrest. In certain embodiments, the item of apparel is a jacket, a pair of biking shorts, a biking shoe, a biking jersey, an exercise suit, a sports bra, spandex pants, under garments, a pair of shorts, a top, a shirt, a glove, a shoe, a boot, a ski boot, a roller skate, an ice skate, a roller blade, a sock, a wrist band, a heart monitor, a wrist watch, a uniform, a baseball cap, a golf cap, a visor, a head band, a hat, glasses, sunglasses, a pair of headphones, a medallion, a pendant, an item of jewelry, a necklace, a bracelet, an anklet, a chemical suit, a bio suit, a space suit, a space helmet, a bullet-proof vest, a fire protection suit, motorcycle leathers, goggles, a hard hat, a construction helmet, a welding mask, a motor racing helmet, a motor cycle helmet, a motor racing suit, motor racing under garments, a bicycle helmet, a sports helmet, a ski suit, long underwear, a riding helmet, an equestrian riding helmet, a fencing mask, a fencing tunic, a shin guard, a knee pad, a military equipment hat, a neck wrap, and a military helmet, among others.

Figure 8:
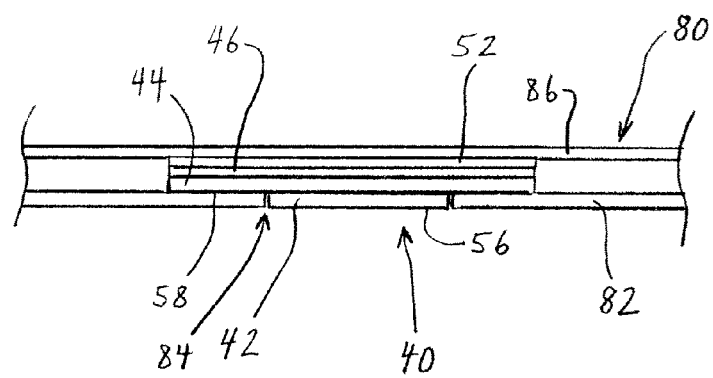
FIG. 8 is a schematic cross-sectional view of an item of apparel that includes a device for heating or cooling a body of a wearer, in accordance with an embodiment of the invention.

The device 40 may be positioned at any location within the item of apparel. For example, the device 40 may be positioned in interior portions of the apparel and/or at one or more outer surfaces of the apparel. Referring to FIG. 8, in one embodiment, the device 40 is positioned within an item of apparel 80 such that the cold side 56 of the TEM 42 contacts the user when the apparel 80 is worn by the user. An inner layer 82 of fabric (e.g., cotton and/or polyester fabric) or other material covers the dry side 58 of the heat sink 44 and includes an opening 84 for the TEM 42. In the depicted embodiment, the apparel 80 includes an outer layer 86 of fabric covering the heat sink 44, wetting material 46, and binding layer 52. The outer layer 86 of fabric is preferably porous or breathable to allow evaporated cooling liquid to pass through the outer layer 86 to the surrounding air. In alternative embodiments, the apparel 80 includes one or more layers of fabric (e.g., the inner layer 82 of fabric) or other material positioned between the cold side 56 of the TEM 42 and the user. In one embodiment, the apparel 80 does not include the outer layer 86 so that the binding layer 52 and/or the wetting material 46 are directly exposed to the surrounding air. In certain embodiments, the item of apparel 80 includes one or more layers of insulation or padding. Examples of insulating materials include neoprene, ethylene vinyl acetate (EVA), and foam materials.

Figure 9:
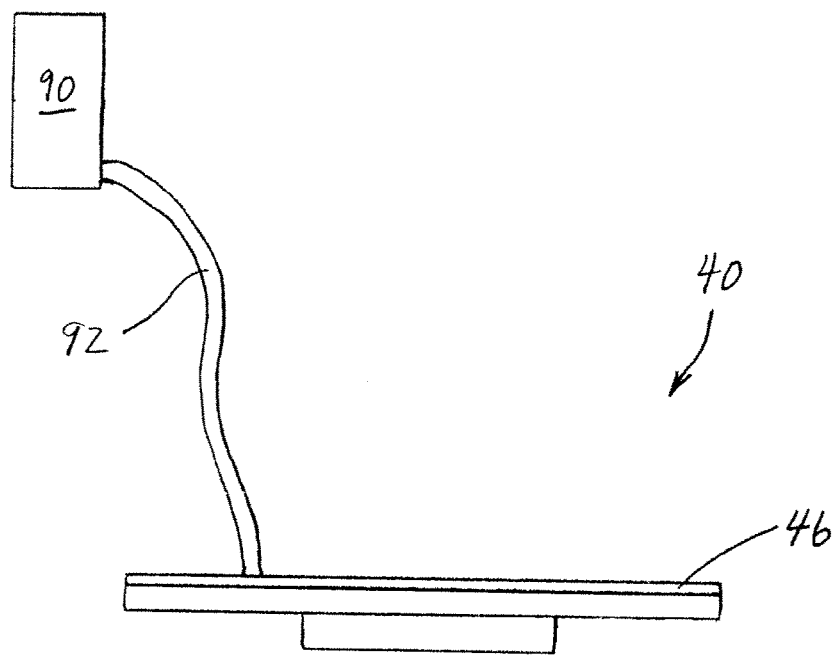
FIG. 9 is a schematic side view of a device for heating or cooling a body of a wearer that includes a supply tank and a supply line, in accordance with an embodiment of the invention.

Referring to FIG. 9, in certain embodiments, the device 40 also includes a supply tank 90 and a supply line 92. The supply tank 90 is configured to contain the cooling liquid, such as water. The supply line 92 is configured to deliver the cooling liquid from the supply tank 90 to the wetting material 46. The supply line 92 may include or consist of a tube and/or a wicking material, such as a hydrophilic fabric or foam. In certain embodiments, the supply tank 90 and/or the supply line 92 are secured to one or more surfaces of the item of apparel 80. For example, the supply tank 90 may be secured to an inner surface of a cooling jacket. Referring again to FIG. 8, the supply line 92 may be disposed between the inner layer 82 and the outer layer 86 of the apparel 80.

In alternative embodiments, the cooling liquid is introduced directly to the wetting material without the use of a supply tank and/or a supply line. For example, the cooling liquid may be introduced by spraying or dripping the cooling liquid onto the wetting material or initially dipping the wetting material into liquid. In an elbow pack or knee pack application, for example, the cooling liquid may be sprayed onto the wetting material about every 15 minutes.

In certain embodiments, when a supply tank and/or a supply line are not utilized, a thickness of the wetting material 46 may be increased so that it may hold an additional amount of cooling liquid. For example, the wetting material 46 may include extra layers of tissue paper and/or cotton. In one embodiment, the wetting material 46 includes a layer of cotton on top of layers of tissue paper. The cotton layer is configured to hold additional cooling liquid so that evaporative cooling may occur for a greater length of time after water has been applied to the device 40.

During operation of the device 40, electrical current is introduced to the TEM 42 using the controller 48 and/or a power supply. As electrical energy is consumed in the TEM 42, heat flows from the cold side 56 of the TEM 42 to the hot side 49 of the TEM 42, thereby creating a temperature difference between the cold and hot sides 56, 49. To provide cold side temperatures that are suitable for cooling applications, it is generally necessary or desirable to dissipate heat from the heat sink 44 attached to the hot side 49 of the TEM 42 using evaporative cooling techniques, rather than relying simply on convective heat transfer mechanisms.

In various embodiments, evaporative cooling is used to remove heat from the hot side 49 of the device 40 by evaporating the cooling liquid from the wetting material 46 disposed on the heat sink 44. For example, the wetting material 46 may be soaked with the cooling liquid, and the cooling liquid may evaporate from the wetting material 46. Rates of evaporation of the cooling liquid generally depend on the temperatures of the heat sink 44 and the cooling liquid, the concentration of evaporated cooling liquid in the surrounding air (e.g., relative humidity), and the amount of convection or air flow in the vicinity of the device 40. For example, the rate of evaporation generally increases as the temperature (and vapor pressure) of the cooling liquid increases. Likewise, the rate of evaporation generally increases when the humidity decreases and/or when the air flow in the vicinity of the device 40 increases.

The cooling liquid may be any liquid capable of providing the desired rate of evaporative cooling. For example, the cooling liquid may include or consist of water, alcohol (e.g., ethanol), and/or ammonia. In one embodiment, the cooling liquid includes DNA and/or a super polymer having hydrogen bonds that break with the application of heat, thereby absorbing the heat and cooling the device.

In certain embodiments, the cooling liquid includes a fragrance. As the cooling liquid evaporates from the wetting material 46, the fragrance may provide aromatherapy.

Figure 10:
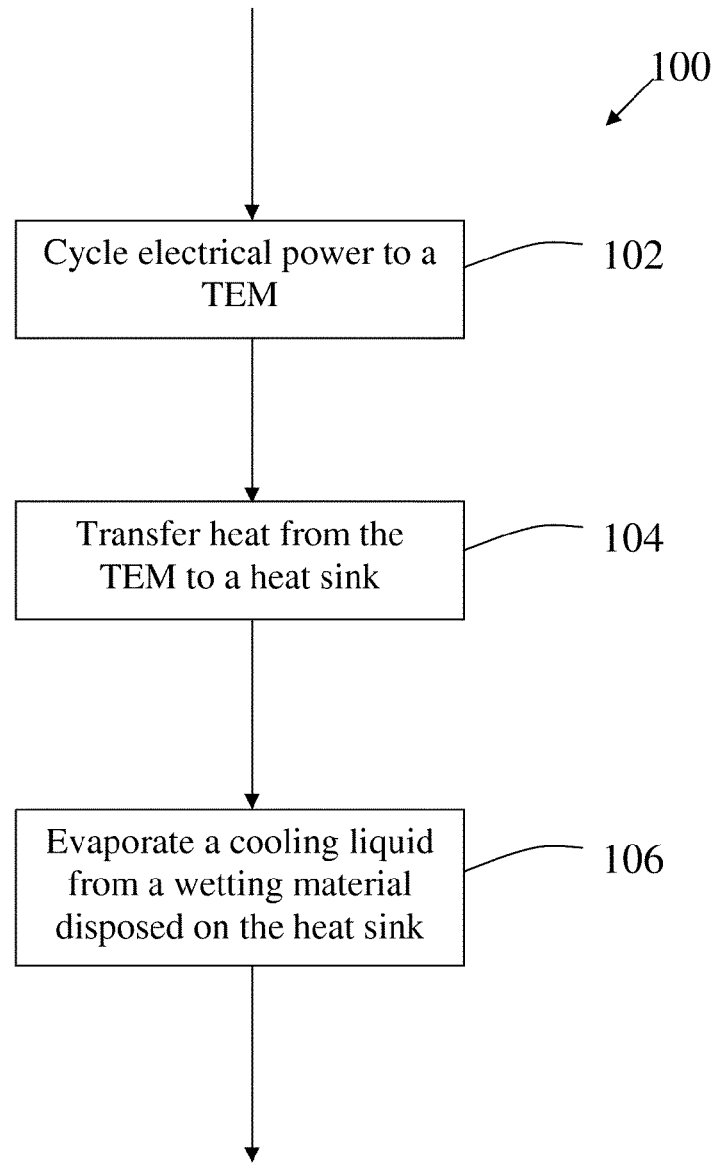
FIG. 10 is a flowchart of a method for heating or cooling a portion of a body of a wearer.

FIG. 10 is a flowchart of a method 100 of cooling a portion of a body of a user, in accordance with various embodiments of the invention. The method 100 includes cycling (step 102) electrical power to a TEM at a duty cycle of at least about 10%. Heat is transferred (step 104) from a hot side of the TEM to a heat sink attached to the TEM. Heat from the heat sink causes a cooling liquid to evaporate (step 106) from a wetting material disposed on the heat sink, thereby cooling the heat sink and the TEM. The evaporated cooling liquid enters the surrounding air. Through the evaporative cooling, a temperature of the hot side and the cold side of the TEM may be maintained at lower temperatures and, accordingly, the device can operate at relatively high duty cycles (e.g., greater than about 10%, 20%, 30%, 40%, 50%, 60%, 70%, 80%, 90% up to about 100%).

In certain embodiments, the hot side of the TEM is maintained well below 100° C., such that the cooling liquid does not boil and the corresponding rate of evaporation is not excessive. Typical evaporation rates for the cooling liquid are from about 1 ml/hour to about 120 ml/hour, or from about 2 ml/hour to about 60 ml/hour. With these rates of evaporation, the wetting material may hold enough cooling liquid for about 10 minutes to about eight hours of evaporative cooling, depending on the ambient temperature and vapor concentrations (e.g., humidity). For example, in one embodiment, a supply tank holding 8 ml of water provides four hours of continuous cooling for a single TEM device in a jacket. In another embodiment, a jacket includes multiple TEM devices (e.g., up to about 30). About 8 ml of cooling liquid may be stored in the wetting material and/or supply tank for each of the TEM devices (e.g., about 80 ml stored for 10 TEM devices). In certain embodiments, 20 ml of water provides about 20 minutes of cooling for a knee pack. The wetting material may be replenished with cooling liquid, as needed.

In certain embodiments, a heat transfer rate Q associated with heating or cooling the object is from about 0.2 W to about 200 W, or from about 0.5 W to about 50 W. A temperature of a cold side of the TEM may be, for example, from about −10° C. to about 30° C., or from about 0° C. to about 20° C. In one embodiment, the temperature of the cold side is about 11° C. For example, in an elbow pack application, a knee pack application, a cooling jacket application, and a neck wrap application, the cold side temperature may be maintained from about 10° C. to about 12° C., from about 4° C. to about 6° C., from about 16° C. to about 17° C., and from about 17° C. to about 18° C. A temperature of the hot side of the TEM may be, for example, from about 30° C. to about 80° C., or from about 40° C. to about 60° C. In one embodiment, the temperature of the hot side of the TEM is about 45° C. TEM surface temperatures may generally depend on the amount of electrical power, the heat sink geometry, and ambient conditions.

In certain embodiments, heat transfer rates due to evaporative cooling of the cooling liquid from the wetting material are equal to or greater than the heat transfer rates due to either radiative heat transfer or convective heat transfer. For example, in one embodiment, the rate of evaporative cooling with no forced air flow is equal to or greater than the rate of convective heat transfer with forced air flow.

In another implementation, the devices described herein are used to heat the body of the wearer. In this embodiment, the hot side of the TEM is positioned towards the body of the wearer, and heat generated by the TEM is transferred to the body of the wearer. Evaporative cooling at the heat sink may not be necessary with this implementation, though a flexible or padded heat transfer plate, mesh, foil or other material (wet or dry) may be used to increase the effective area of the thermal transfer to the body and permit contoured coupling to the body curvature to provide effective, comfortable heat distribution over a relatively large area, if desired. Similar structure may be provided to increase the heat transfer area from the body in a cooling application.

In various embodiments, the devices described herein are configured to provide electrical stimulation to the body part of the user. The electrical stimulation may be provided to the body part in addition to heating or cooling the body part, as described above. Alternatively, the electrical stimulation may be provided without heating or cooling the body part. In one embodiment, to provide the electrical stimulation, the device includes an electrode in electrical communication with the body part. The electrical stimulation may be delivered to the body part at a steady rate and/or it may be delivered intermittently. In certain embodiments, the electrical stimulation includes an electrical current from about 0.5 milliamps to about 500 milliamps, or from about 1 milliamp to about 100 milliamps. For example, the electrical current may be about 4 milliamps. In one embodiment, the electrical stimulation is cycled at a period of from about 0.1 minutes to about 60 minutes, or from about 5 minutes to about 10 minutes. In certain embodiments, the electrical stimulation includes electrical pulses having a frequency of about 100 Hz, or up to about 200 Hz. A pulse width for the electrical stimulation may be about 100 microseconds, or up to about 500 microseconds.

Values for various parameters associated with certain embodiments of the devices and methods described herein are summarized in Table 1, though values outside these ranges are contemplated and are to be considered within the scope of the invention.

TABLE 1

Parameter values for heating and cooling devices.

| Parameter | Typical Value | Min. Value | Max. Value |
| --- | --- | --- | --- |
| TEM Surface Area, $A_M$ (mm$^2$) | 450-900 | 100 | 2000 |
| TEM Thickness, $T_M$ (mm) | 4.0 | 1 | 10 |
| TEM Cooling Capacity (W) | 25 | 0.1 | 50 |
| TEM Voltage (V) | 7.4 | 2 | 35 |
| TEM Current (A) | 1.7 | 0.2 | 5 |
| Heat Sink Thickness, $T_H$ (mm) | 2 | 1 | 15 |
| Heat Sink Surface Area, $A_H$ (mm$^2$) | 2500 | 100 | 10000 |
| Heat Sink Bend Angle, $\theta$ (degrees) | 30-45 | 0 | 90 |
| Etching Agent Exposure Time (minutes) | 15 | 1 | 100 |
| Wetting Material (tissue/cotton layers) | 10 | 1 | 20 |
| Cold Side Temperature (° C.) | 11 | −10 | 30 |
| Hot Side Temperature (° C.) | 45 | 30 | 80 |
| Duty Cycle, D (%) | 97 | 10 | 100 |
| Heating/Cooling Period, T (minutes) | 3 | 1 | 10 |
| Heat Transfer Rate, Q (W) | 0.5-50 | 0.2 | 200 |
| Current for Electrical Stimulation (mA) | 4 | 0.5 | 500 |
| Electrical Stimulation Period (minutes) | 5-10 | 0.1 | 60 |
| Frequency of Electrical Pulses (Hz) | 100 | 0 | 200 |
| Pulse Width (micro seconds) | 100 | 0 | 500 |

In certain embodiments, the devices and methods described herein are used to treat a wide variety of ailments. Examples of ailments that may be treated include, for example, arthritis, tennis elbow, golf elbow, migraine headaches, menstrual pain, back pain, ankle sprains, sore muscles, and sore joints. The devices may also be used to improve the comfort level of the user. For example, the devices may be used to keep the user cool on a hot day, or keep the user warm on a cold day. Any combination of heating and/or cooling may be utilized. For example, the devices may be used to heat a body part for 30 minutes, and then cool the body part for 30 minutes.

EXAMPLES

To evaluate the cooling performance of the devices described herein, a device having a TEM, a heat sink, a wetting material, and a binding layer was mounted to a water-filled, insulated chamber, such that a cold side of the TEM was in contact with the water inside the chamber. The device and the chamber were placed inside a box in which the ambient temperature and humidity could be controlled, as desired. The temperature of the water in the water-filled chamber was used as an indication of the rate of cooling achieved by the device. For example, the greater the measured rate of decrease in water temperature, the greater the rate of cooling achieved by the device.

Figure 11:
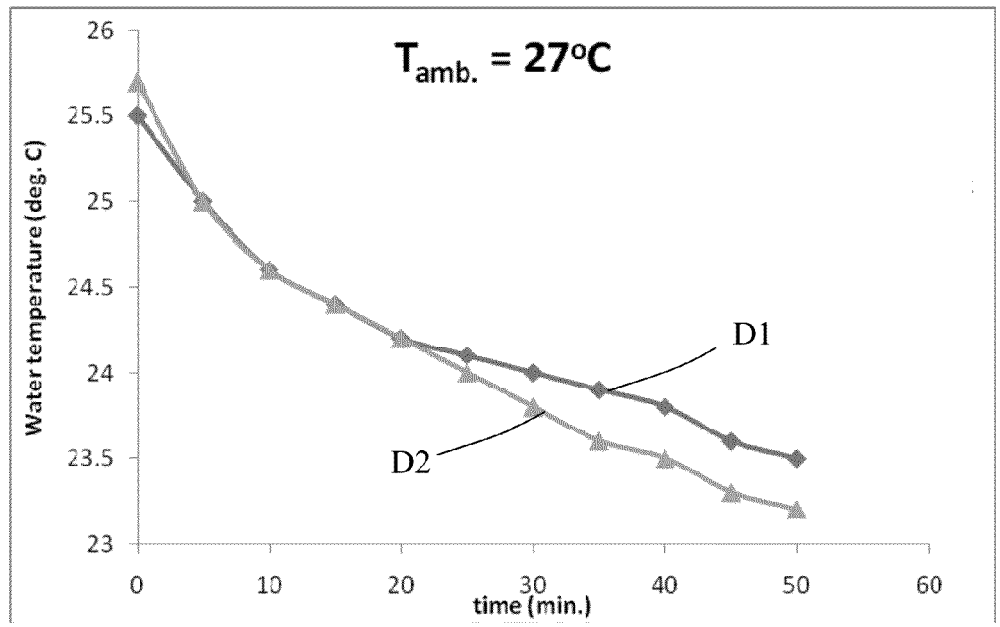
FIGS. 11 through 13 are plots of water temperature versus time, in accordance with an embodiment of the invention.
Figure 12:
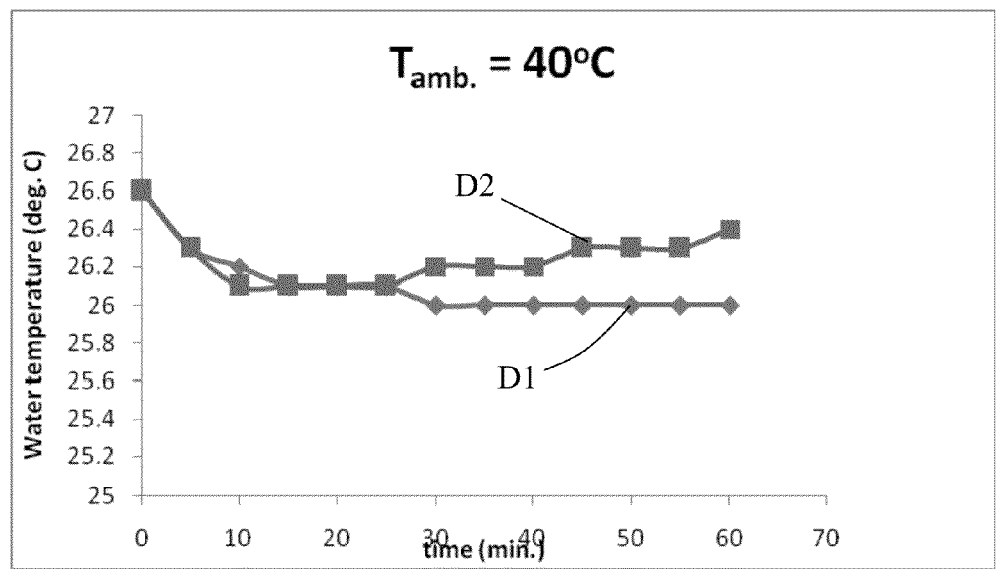

FIGS. 11 and 12 are plots of water temperature versus time for the device and for a fan-cooled device, in accordance with certain embodiments of the invention. During the test, the device was cooled by evaporative cooling, as described above, using water as the cooling liquid. By contrast, the fan-cooled device, which included a TEM, a heat sink, and a fan mounted to the heat sink, was cooled by forced convection (i.e., no evaporative cooling) due to air flow of approximately 1 m/s over the heat sink from the fan. The results in FIGS. 11 and 12 indicate that the rate of cooling obtained with the device (curve D1) was about the same as the rate of cooling obtained with the fan-cooled device (curve D2) up to about 20 minutes to 25 minutes. Thereafter, the wetted device (curve D1) showed better cooling under higher ambient temperature conditions. For the results in FIGS. 11 and 12, the ambient temperature was 27° C. and 40° C., respectively, and the relative humidity was 70%.

Figure 13:
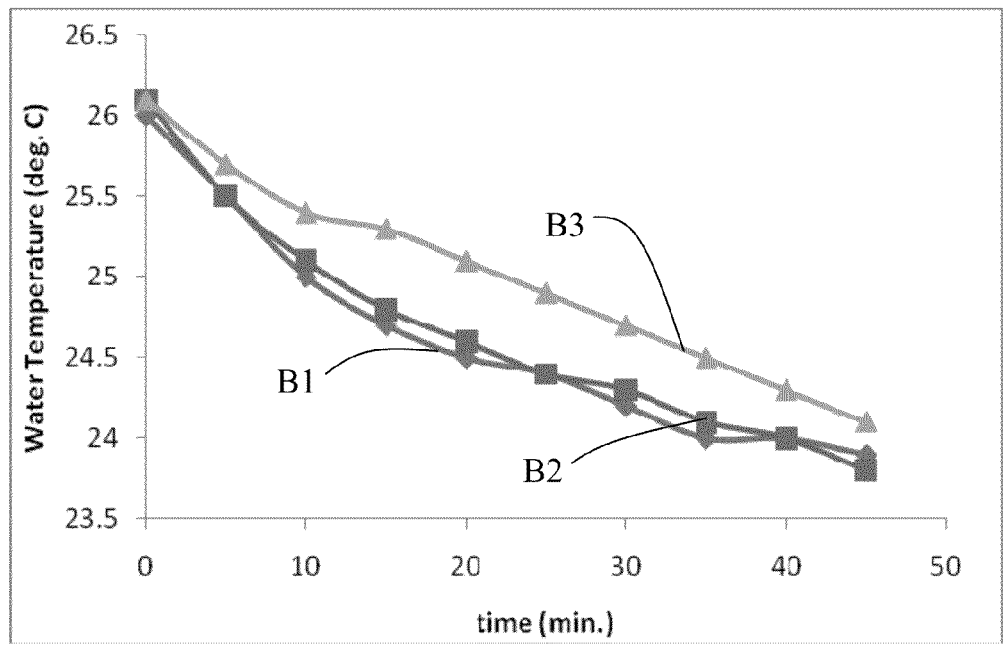

FIG. 13 is a plot of water temperature versus time that illustrates the influence of a heat sink bend angle on the rate of cooling, in accordance with certain embodiments of the invention. The results show that the rate of cooling was generally about the same for bend angles of 10-15 degrees (curve B1) and about 20-25 degrees (curve B2). The rate of cooling was observed to be lower for a bend angle of about 40-45 degrees (curve B3).

Figure 14:
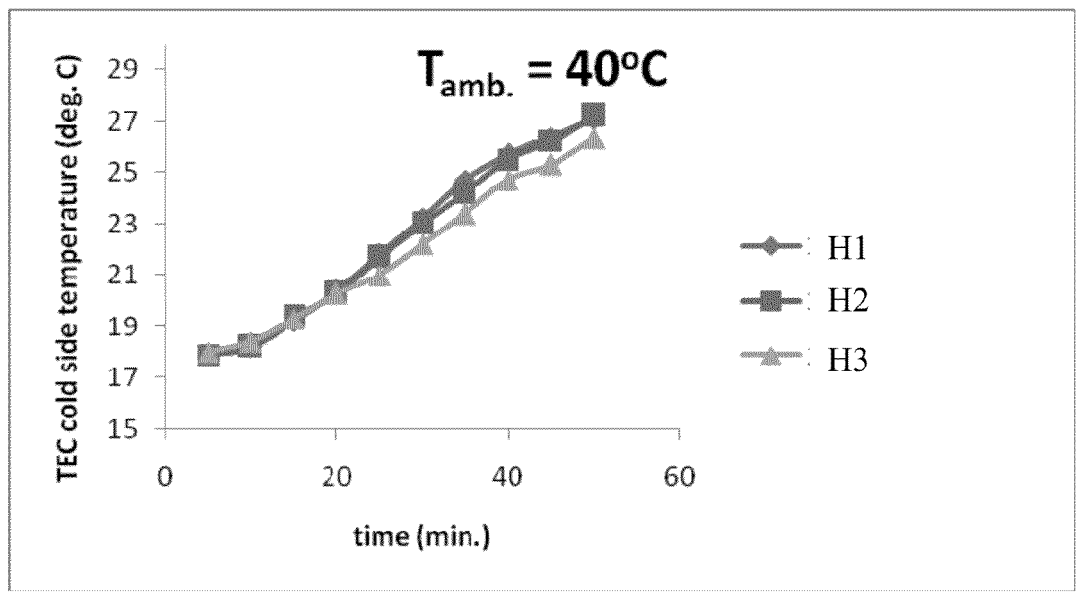
FIGS. 14 and 15 are plots of a cold side of a thermoelectric device versus time, in accordance with an embodiment of the invention.

FIG. 14 is a plot of the temperature of a cold side of a device (i.e., the cold side of a TEM) versus time, in accordance with certain embodiments. Three different aluminum heat sinks were tested to obtain the data for this figure. Curves H1, H2, and H3 show the results for a 1 mm thick heat sink, a 1.5 mm thick heat sink, and a 1.5 mm thick heat sink having a black coating (i.e., black paint). All other parameters for the heat sinks were the same. To perform the test, 1.5 ml of water was poured onto each heat sink and the ambient temperature was maintained at around 40° C. The results in the figure show that the heat sink with the black coating (curve H3) produced the coldest temperatures and therefore performed the best, perhaps due to a higher emissivity and more radiative heat transfer. Separate test results indicated that a heat sink with a thickness of about 1.5 mm provided excellent results.

Figure 15:
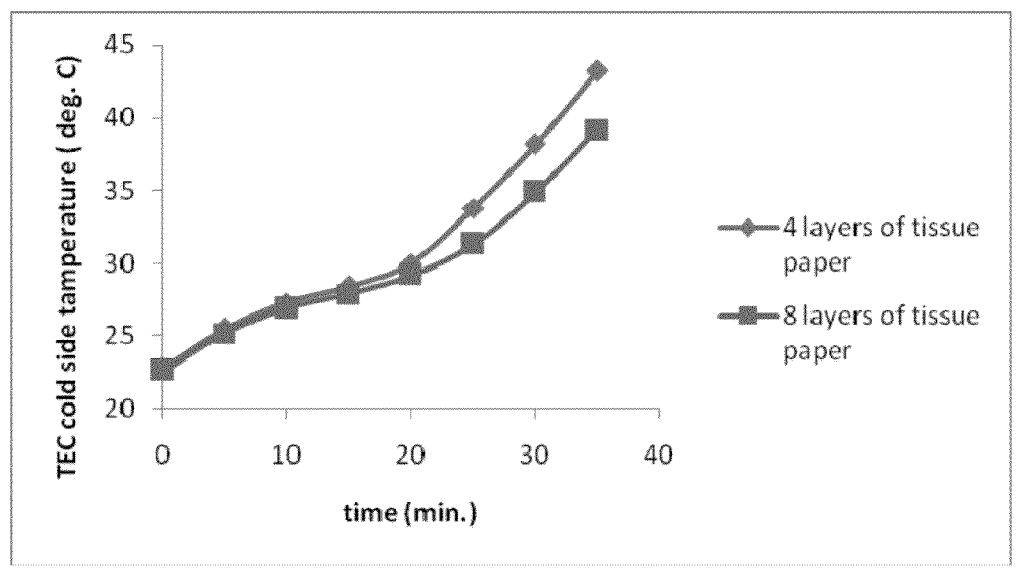

FIG. 15 is a plot of the temperature of a cold side of a device versus time for different amounts of wetting material, in accordance with certain embodiments. As indicated, the cold side temperature was observed to be lower with eight layers of tissue paper than with four layers of tissue paper. The tissue paper in this test had a thickness of about 0.1 mm.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A device for heating or cooling a body of a user, the device comprising:
    a thermoelectric module;
    a heat sink thermally coupled to a surface of the thermoelectric module;
    a wetting material in thermal communication with the heat sink; and
    a controller for cycling the thermoelectric module in accordance with a duty cycle greater than 10% and a cycle time from about 1 minute to about 10 minutes, the cycle time enhancing the user's perception of the heating or cooling.

2. The device of claim 1, further comprising:
    a supply tank; and
    a supply line connecting the wetting material and the supply tank, wherein the supply line comprises a wicking material to convey a liquid from the supply tank to the wetting material.

3. The device of claim 1, wherein the heat sink comprises a thickness from about 1 mm to about 15 mm.

4. The device of claim 1, further comprising a binding layer securing the wetting material to the heat sink, the binding layer wrapped around an outer edge of the heat sink, wherein the wetting material is disposed between the heat sink and the binding layer.

5. The device of claim 1, wherein the heat sink comprises at least one of (i) an etched surface and (ii) a contoured surface, wherein the contoured surface forms a bend.

6. The device of claim 1, wherein the wetting material comprises at least one of (i) an antimicrobial agent and (ii) a hydrophilic material.

7. The device of claim 1, wherein the wetting material comprises a thickness from about 1 mm to about 3 mm.

8. The device of claim 1, wherein the wetting material comprises at least one of (i) tissue and (ii) cotton.

9. The device of claim 1, further comprising a battery and a switched electrical connection.

10. The device of claim 1, wherein the device is integrated into apparel, wherein the apparel is selected from the group consisting of a neck wrap, an elbow pack, a knee pack, a back pack, an ankle pack, a universal pack a heating jacket, a cooling jacket, a heating-cooling jacket, an anti-bleeding pack, a head band, an abdominal pad, a shoe insole, clothing, footwear, a car seat, and a helmet.

11. The device of claim 1, wherein the thermoelectric module comprises a heating surface area from about 100 mm$^2$ to about 2000 mm$^2$.

12. The device of claim 4, wherein the binding layer comprises an aluminum mesh.

13. The device of claim 1, wherein the heat sink is characterized by an absence of fins.

14. The device of claim 1, wherein the heat sink comprises an etched surface, to increase surface area for heat transfer from the heat sink.

15. A method of heating or cooling a portion of a body of a user, the method comprising the steps of:
    cycling electrical power to a thermoelectric module at a duty cycle of at least 10% and a cycle time from about 1 minute to about 10 minutes, the cycle time enhancing the user's perception of the heating or cooling;
    transferring heat from the thermoelectric module to a heat sink; and
    evaporating a liquid from a wetting material disposed on the heat sink, wherein the evaporated liquid enters the surrounding atmosphere.

16. The method of claim 15, further comprising conveying the liquid from a supply tank to the wetting material through a supply line.

17. The method of claim 15, further comprising applying the liquid to the wetting material.

18. The method of claim 15, wherein cycling electrical power comprises at least one of (i) a duty cycle from about 30% to about 100% and (ii) a cycle time from about 2 minutes to about 5 minutes.

19. The method of claim 15, wherein transferring heat from the thermoelectric module comprises a heat transfer rate from about 0.2 W to about 200 W.

20. The method of claim 15, wherein evaporating the liquid provides a heat transfer rate from about 0.2 W to about 200 W.

21. The method of claim 15, wherein a cold side of the thermoelectric module comprises a temperature from about −10 degrees C. to about 30 degrees C.

22. The method of claim 15, wherein the heat sink temperature is at least about 30 degrees C.

23. The method of claim 15, wherein the method comprises treating at least one of arthritis, tennis elbow, golf elbow, a migraine headache, menstrual pain, back pain, and an ankle sprain.

24. The method of claim 15, further comprising providing electrical stimulation to a user.

25. The method of claim 15, wherein the liquid comprises a fragrance to provide aromatherapy.

26. A method of manufacturing a device for heating or cooling a portion of a body of a user, the method comprising the steps of:
    providing a heat sink;
    etching a surface of the heat sink to increase an effective surface area thereof;
    attaching the heat sink to a thermoelectric module;
    disposing a wetting material over the heat sink;
    securing the wetting material to the heat sink with a binding layer; and
    providing a controller for the thermoelectric module, the controller configured to cycle the thermoelectric module in accordance with a duty cycle greater than 10% and a cycle time from about 1 minute to about 10 minutes, the cycle time enhancing the user's perception of the heating or cooling.

27. The method of claim 26, wherein the wetting material is disposed between the heat sink and the binding layer, the binding layer wrapped around an outer edge of the heat sink.

28. The method of claim 26, further comprising introducing into the heat sink a bend angle.

29. The method of claim 26, further comprising electrically connecting the thermoelectric module to a battery pack.

30. The method of claim 26, further comprising integrating the thermoelectric module into an item of apparel, wherein the item of apparel is selected from the group consisting of a neck wrap, an elbow pack, a knee pack, a back pack, a heating jacket, a cooling jacket, a heating-cooling jacket, an anti-bleeding pack, a head band, an abdominal pad, a shoe insole, clothing, footwear, a car seat, and a helmet.

* * * * *